(12) United States Patent
Pollack et al.

(10) Patent No.: US 8,189,042 B2
(45) Date of Patent: *May 29, 2012

(54) VISION ANALYSIS SYSTEM FOR A PROCESS VESSEL

(75) Inventors: Michael J. Pollack, Landale, PA (US); Branson J. Darnell, Harleysville, PA (US); Steven J. Mandrachia, Eagleville, PA (US); Gary Reichl, Coopersburg, PA (US); Richard A. DiDomizio, Hatfield, PA (US)

(73) Assignee: Pollack Laboratories, Inc., Colmar, PA (US)

( * ) Notice: Subject to any disclaimer, the term of this patent is extended or adjusted under 35 U.S.C. 154(b) by 1141 days.

This patent is subject to a terminal disclaimer.

(21) Appl. No.: 11/955,050

(22) Filed: Dec. 12, 2007

(65) Prior Publication Data

US 2008/0143828 A1 Jun. 19, 2008

Related U.S. Application Data

(60) Provisional application No. 60/870,207, filed on Dec. 15, 2006.

(51) Int. Cl.
*H04N 7/18* (2006.01)
(52) U.S. Cl. .......................... 348/82; 73/234
(58) Field of Classification Search .............. 73/40.7, 73/234; 348/85, 82; 606/41; 114/274; 430/105; 204/232; 436/177; 75/10.61; 382/133
See application file for complete search history.

(56) References Cited

U.S. PATENT DOCUMENTS

| | | | |
|---|---|---|---|
| 3,809,607 A | 5/1974 | Murrey et al. |
| 4,393,466 A | 7/1983 | Deindoerfer et al. |
| 4,659,218 A | 4/1987 | de Lasa et al. |
| 4,814,868 A | 3/1989 | James |
| 4,893,935 A | 1/1990 | Mandel et al. |
| 4,965,601 A | 10/1990 | Canty |
| 4,977,418 A | 12/1990 | Canty |
| 5,152,175 A | 10/1992 | Reynolds |
| 5,182,791 A | 1/1993 | Pollack |
| 5,230,556 A | 7/1993 | Canty et al. |
| 5,425,279 A | 6/1995 | Clark et al. |
| 5,532,389 A | 7/1996 | Trent et al. |
| 5,561,520 A | 10/1996 | Williams |
| 5,956,077 A | 9/1999 | Qureshi et al. |
| 6,047,082 A | 4/2000 | Rhody et al. |
| 6,049,381 A | 4/2000 | Reintjes et al. |
| 6,051,518 A | 4/2000 | Srivastava et al. |
| 6,111,599 A | 8/2000 | Nance et al. |
| 6,122,042 A | 9/2000 | Wunderman et al. |

(Continued)

OTHER PUBLICATIONS

Office Action dated Aug. 9, 2011 issued in co-pending U.S. Appl. No. 11/970,313.

*Primary Examiner* — Le Luu
(74) *Attorney, Agent, or Firm* — Howson & Howson LLP (57) ABSTRACT

A remote vision analysis system for a vessel containing a process liquid having gas bubbles or particles floating therein. A probe extends into the vessel and enables in-situ observation of the process liquid, gas bubbles or particles, and/or surfaces within the vessel. The probe has a proximal end that includes a camera for recording still or motion images of the process liquid, gas bubbles or particles, and/or surfaces within the vessel. An elongate distal end of the probe extends within an interior of the vessel and is housed within a hermetically sealed protective shroud having a lens, or window, through which images are recorded by the camera. The probe is modular and includes interchangeable parts.

20 Claims, 5 Drawing Sheets

U.S. PATENT DOCUMENTS

| | | |
|---|---|---|
| 6,134,342 A | 10/2000 | Doke et al. |
| 6,252,980 B1 | 6/2001 | Schwartz et al. |
| 6,438,261 B1 | 8/2002 | Moshe et al. |
| 6,450,655 B1 | 9/2002 | Walck et al. |
| 6,603,117 B2 | 8/2003 | Corrado et al. |
| 6,629,449 B1 | 10/2003 | Kline-Schoder et al. |
| 6,660,995 B1 | 12/2003 | Canpolat et al. |
| 6,673,532 B2 | 1/2004 | Rao |
| 6,723,981 B2 | 4/2004 | Corrado et al. |
| 6,782,184 B2 | 8/2004 | Canty et al. |
| 6,806,900 B2 | 10/2004 | Eversole et al. |
| 6,849,308 B1 | 2/2005 | Speakman et al. |
| 6,888,631 B2 | 5/2005 | Eriksson |
| 6,960,756 B1 | 11/2005 | Penumadu et al. |
| 7,041,493 B2 | 5/2006 | Rao |
| 2002/0101508 A1 | 8/2002 | Pollack |
| 2003/0150716 A1* | 8/2003 | Hua et al. .................. 204/232 |
| 2004/0004660 A1* | 1/2004 | Mandal et al. ................ 348/85 |
| 2004/0036859 A1 | 2/2004 | Silverman et al. |
| 2004/0095577 A1 | 5/2004 | Eckardt et al. |
| 2004/0186469 A1* | 9/2004 | Woloszko et al. ............. 606/41 |
| 2005/0046841 A1 | 3/2005 | Rabinski et al. |
| 2005/0130317 A1* | 6/2005 | Ventzki et al. ................ 436/177 |
| 2005/0134845 A1 | 6/2005 | Bordelon |
| 2005/0199818 A1 | 9/2005 | Tomita et al. |
| 2006/0017930 A1 | 1/2006 | Canty et al. |
| 2006/0117837 A1* | 6/2006 | Voglsinger .................... 73/40.7 |
| 2006/0152730 A1 | 7/2006 | Schneider |
| 2006/0222980 A1* | 10/2006 | Makino et al. ................ 430/105 |
| 2006/0256340 A1 | 11/2006 | Hansen et al. |
| 2007/0155985 A1 | 7/2007 | Wonders et al. |
| 2007/0155986 A1 | 7/2007 | Wonders et al. |
| 2007/0208194 A1 | 9/2007 | Woodruff et al. |
| 2008/0092692 A1* | 4/2008 | Sahajwalla .................. 75/10.61 |
| 2008/0141921 A1* | 6/2008 | Hinderks ...................... 114/274 |
| 2008/0166037 A1* | 7/2008 | Mandrachia et al. ......... 382/133 |

\* cited by examiner

VISION ANALYSIS SYSTEM FOR A PROCESS VESSEL

CROSS-REFERENCE TO RELATED APPLICATION

This application claims the benefit under 35 USC §119(e) of U.S. Provisional Patent Application No. 60/870,207, filed Dec. 15, 2006.

BACKGROUND OF THE INVENTION

The present invention relates to a system of observing a process occurring within a sealed or open vessel, and more particularly, the present invention relates to a remote vision system that records images of a process liquid, bubbles or particles in the liquid, and surfaces within the vessel.

The production of biopharmaceuticals, enzymes and other biotechnology derived compounds typically takes place in a vessel, such as a bioreactor, fermenter, or the like. Such vessels may include a sparger for introducing a gas, such as compressed air, directly within the liquid in the form of bubbles. The bubbles must be of an appropriate size and volume and be injected at an appropriate rate into the process liquid so that the gas can be absorbed uniformly throughout the process liquid before reaching the surface of the liquid. Such vessels also typically include an agitator provided as one or more rotating blades.

Problems can arise with respect to the injection of gas into the process liquid. For example, if the size, volume, quantity, or injection rate of bubbles and/or parameters, such as bubble size versus volume, is too great, a significant quantity of the bubbles will reach the surface of the process liquid without being absorbed and will create an undesirable amount of foam in the headspace of the vessel. The presence of too much foam can effectively close off the upper surface of the process liquid, thereby starving the culture of oxygen, and/or can clog filters. Problems can also occur if the size, volume, quantity, or injection rate of bubbles and/or parameters, such as bubble size versus volume, is too small. In this case, only localized areas of the process liquid will be sufficiently aerated and an overall sufficient amount of absorption and uniform absorption will fail to occur.

Problems are also presented by the agitator. The agitator can function to shear the bubbles to smaller sizes and to distribute gas bubbles by creating turbulence. An agitator can also create partial vacuums within the process liquid and generate air bubbles via cavitation thereby pulling air into the process liquid from the headspace. If the blades of the agitator rotate too swiftly, bubbles of an undesirable large size may be generated, too much turbulence may be generated, and too much foam may be caused to form in the headspace. Thus, an appropriate amount of agitation must be utilized to accomplish specific objectives of a given process and to strike a desired balance between aeration as a result of the output of the sparger versus aeration as a result of cavitation.

Adjustments to the quantity, volume, bubble size, bubble size versus volume, and rate of gas introduced into a process liquid and to the speed of rotation of the agitator within a vessel are typically made based on past experiences, objective parameters, and yields, and not by direct observation. Further problems experienced with respect to processes in vessels relate to real time verification of mechanical operation of parts within the vessel and the cleanliness, or lack thereof, of the vessel and any internal parts.

An example of a monitoring system for a hostile environment is disclosed in U.S. Patent Application Publication No. 2002/0101508 A1 of Pollack, and an example of a probe for transmitting light through a fluid is disclosed by U.S. Pat. No. 5,182,791 issued to Pollack. Also see U.S. Patent Application Publication No. 2006/0017930 A1 of Canty et al. and U.S. Pat. Nos. 6,450,655 B1 of Walck et al., 6,782,184 B2 and 5,230,556 of Canty et al., 4,977,418 and 4,965,601 issued to Canty, 6,888,631 B2 issued to Eriksson, 5,956,077 issued to Qureshi et al. and 6,111,599 of Nance et al. for other inspection methods and apparatus.

While the monitoring and inspection systems disclosed by the above referenced patents may function in an acceptable manner, there continues to be a need for improved systems and methods enabling real time in-situ observation of processes being performed in process vessels.

BRIEF SUMMARY OF THE INVENTION

The present invention is a remote vision analysis system for a vessel. The vision system can be used to characterize a vessel before proceeding with a process or can be used in-process with a vessel containing a process liquid having gas bubbles or particles entrained therein. A probe extends into the vessel and enables in-situ observation of the process liquid, gas bubbles or particles, and/or surfaces within the vessel. The proximal end of the probe includes a camera for recording still or motion images of the process liquid, gas bubbles or particles, and/or surfaces within the vessel. The probe has an elongate distal end that extends within an interior of the vessel and that is housed within a hermetically sealed protective shroud. The distal end has a lens, or window, through which images are recorded by the camera.

According to one contemplated embodiment of the present invention, a sparger and an agitator are located within the vessel. The sparger releases gas in the form of bubbles directly into the process liquid, and the agitator distributes and shears the bubbles and may generate additional bubbles via cavitation. At least one vision probe monitors bubble characteristics so that adjustments can be made to the process, such as adjustments to the operation of the sparger and agitator, in real time to achieve a desired result.

The distal end of the probe of the present invention carries a means for projecting light within the vessel so that images recorded by the camera can be taken front lit, back lit, or both, and the camera is set up to transfer information of the recorded images to a computer processor having image recognition and analysis software. The software analyzes the images thereby providing observation, verification, and recording of data of the physical changes occurring within the vessel during a production process or testing procedure. The information provided by the software can be used as a control tool to implement changes to process operating parameters in real time.

The probes are of modular construction permitting parts of the probe, such as the camera, lens system, lighting, etc., to be interchangeable and moveable to different probe access ports in the vessel or to within an open top or other opening of the vessel. Shrouds can be put into several ports of the vessel prior to filling the vessel. Shrouds can also be positioned within an open top of an unsealed vessel and held in place by a bracket or the like. This permits camera lenses and lighting systems to be moved from shroud to shroud which expands vision monitoring capability while minimizing cost due to duplication of camera, lens, and lighting components.

According to another aspect of the present invention, a method of analyzing bubbles or particles in a process liquid contained in a vessel is provided. Gas in the form of bubbles is released from a sparger in the process liquid within the vessel and the gas bubbles are sheared and distributed within the process liquid via an agitator. The gas bubbles are observed in-situ with a probe extending within the vessel.

Observation of the process liquid and bubbles includes projecting light from the probe into the vessel to illuminate the gas bubbles and recording images of the illuminated bubbles with a camera mounted on the probe. The images are analyzed, preferably in real time, with image recognition and analysis software. For instance, the software can measure bubble size, mean diameter, surface area, flow rate, flow pattern, and/or population distribution. Such information can be used to control a process condition in the sealed vessel.

The probe is sealed from the process liquid via an elongate protective shroud and various components of the probe are interchangeable. For example, the shroud permits movement of components, such as the camera or other sensors, to different access ports in the vessel without disturbing a process being performed in the vessel. This permits camera tenses and lighting systems to be moved from shroud to shroud which expands vision monitoring capability while minimizing costs.

BRIEF DESCRIPTION OF THE DRAWINGS

The features of the present invention should become apparent from the following description when taken in conjunction with the accompanying drawings, in which.

DETAILED DESCRIPTION OF THE INVENTION

Figure 1:
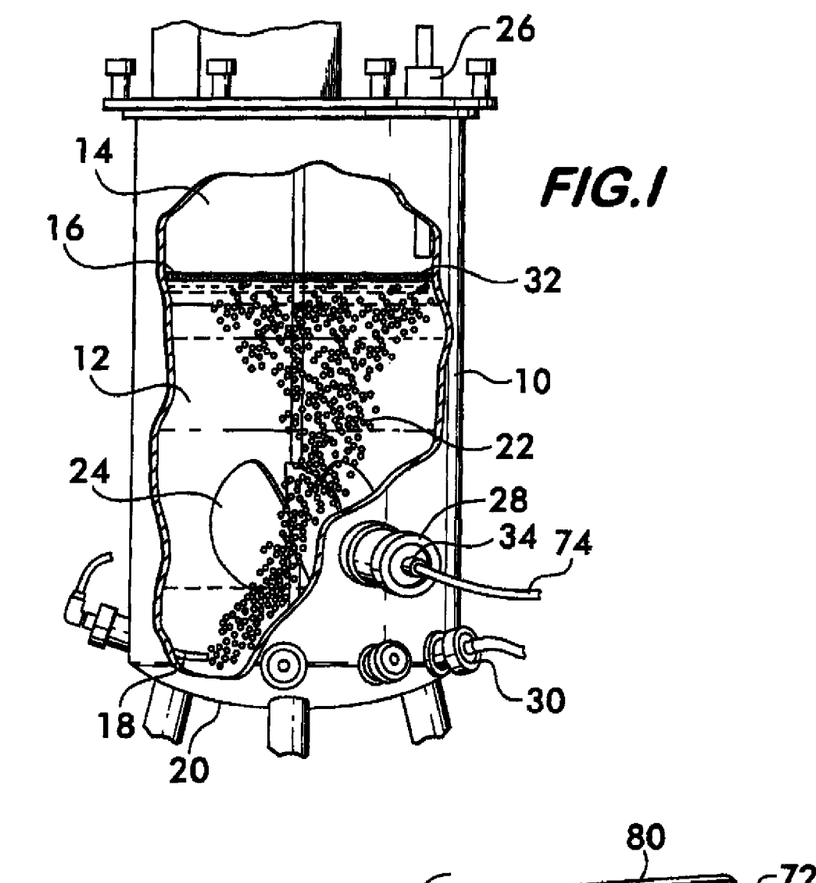
FIG. 1 is a partially-cutaway front elevational view of a sealed vessel having a vision analysis system according to the present invention.

A vessel, tank, or vat 10 is illustrated in FIG. 1. The vessel 10 can be a sealed vessel that is closed at its upper and lower ends, or an unsealed vessel that has, for instance, an open upper end. For purposes of example, the vessel 10 can be a bioreactor or microbial fermenter used in the production of biopharmaceuticals, enzymes or other biotechnology derived compounds. The vessel according to the present invention is not limited to bioreactors and fermenters nor is it limited to the production of the above referenced substances. The present invention is directed to any type of sealed or unsealed vessel in which a process, such as fermentation or the like, is being performed therein.

The illustrated vessel 10 contains a process liquid 12 and defines a headspace 14 located above a surface 16 of the liquid 12. A sparger 18 is located near the base 20 of the vessel 10 and injects a gas, such as compressed air, into the liquid 12. At least a majority of the gas bubbles 22 are intended to be absorbed by the liquid 12 before being able to float to the upper surface 16 of the liquid 12. An agitator 24, such as rotating blades, is located above the sparger 18 to distribute and shear the bubbles 22. The agitator 24 can also be utilized to generate additional bubbles via cavitation, if desired. As an alternative to gas bubbles, other substances, particles or the like can be infused into the process liquid.

The vessel 10 illustrated in FIG. 1 has three access ports, 26, 28 and 30. As will be discussed in greater detail below, access port 26 permits observation and recording of the headspace 14 including the condition of the foam 32 (ie., color, density, bubble size, etc.) located on the surface 16 of the process liquid 12 and the cleanliness of the interior walls and surfaces of the vessel in the headspace area. Observation of the headspace 14 in real time permits anticipation of problems, such as foam blockage of a fermenter vent filter. This enables the user to make adjustments to process parameters during an on-going process to correct and/or prevent such problems.

The access port 28 permits observation of the mechanical motion of the agitator, or impeller, 24, the cleanliness of the agitator 24, as well as various characteristics of the bubbles 22 adjacent the agitator 24 (ie., distribution, reduction, flow rate, flow pattern, etc.). Bioreaction yield is affected by the distribution of bubbles through the liquid. In cell culture, primary agitators are typically axial flow type agitators, and in microbial fermentation, agitators are typically radial flow type agitators. Observation in real time through access port 28 enables problems with respect to gas flooding or cell clumping to be recognized so that corrective adjustments can be made during the process. Accordingly, the observations provided by the present invention permit the present invention to be an analytical tool as well as a process control tool.

The access port 30 permits observation of the operation of the sparger 18 and the characteristics of the bubbles 22 emanating therefrom (ie. size, population, rate, etc.). Cell growth and product expression depend heavily on gas mass transfer. In cell culture, it is useful to know bubble size, gas volume, bubble size as a percent of gas volume, number of bubbles, and rate as a function of gas flow rate through the sparger. In microbial fermentation, it is important to know the bubble size, bubble size as a percent of gas volume, number and rate as function of both gas flow rate and the RPM of the high-shear impeller blades.

Figure 2:
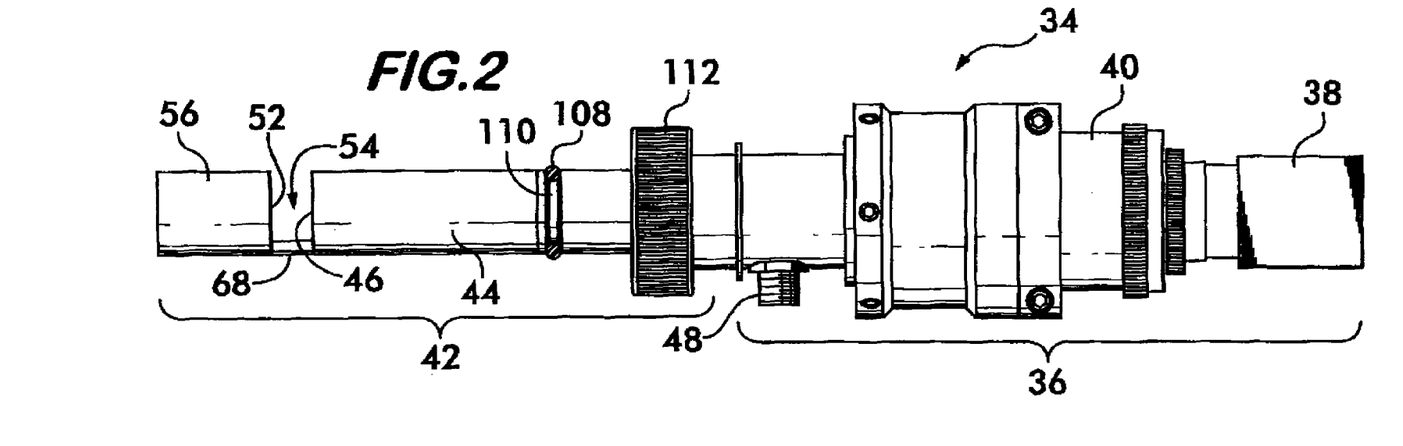
FIG. 2 is a side elevational view of a vision probe according to the present invention.

A vision probe, such as probe 34 illustrated in FIG. 2, can be mounted in any of the above referenced access ports, 26, 28 and 30, or it can simply be mounted via a bracket or the like to extend into an open top of a vessel. A proximal end 36 of the probe includes a camera 38 and an optical lens assembly 40. In most instances, when the vision probe 34 is mounted to the vessel 10 via one of the access ports, 26, 28 and 30, the proximal end 36 including the camera 38 and lens assembly 40 is located on the ambient, or external, side of the wall of the vessel 10. This enables the camera and lens assembly to be in communication with ambient conditions and remain functional despite the hostile environment and temperatures within the vessel. Optionally, the proximal end 36 of the probe 34 can be located within a sealed protective canister 102 (see FIG. 9) within the vessel 10.

Figure 9:
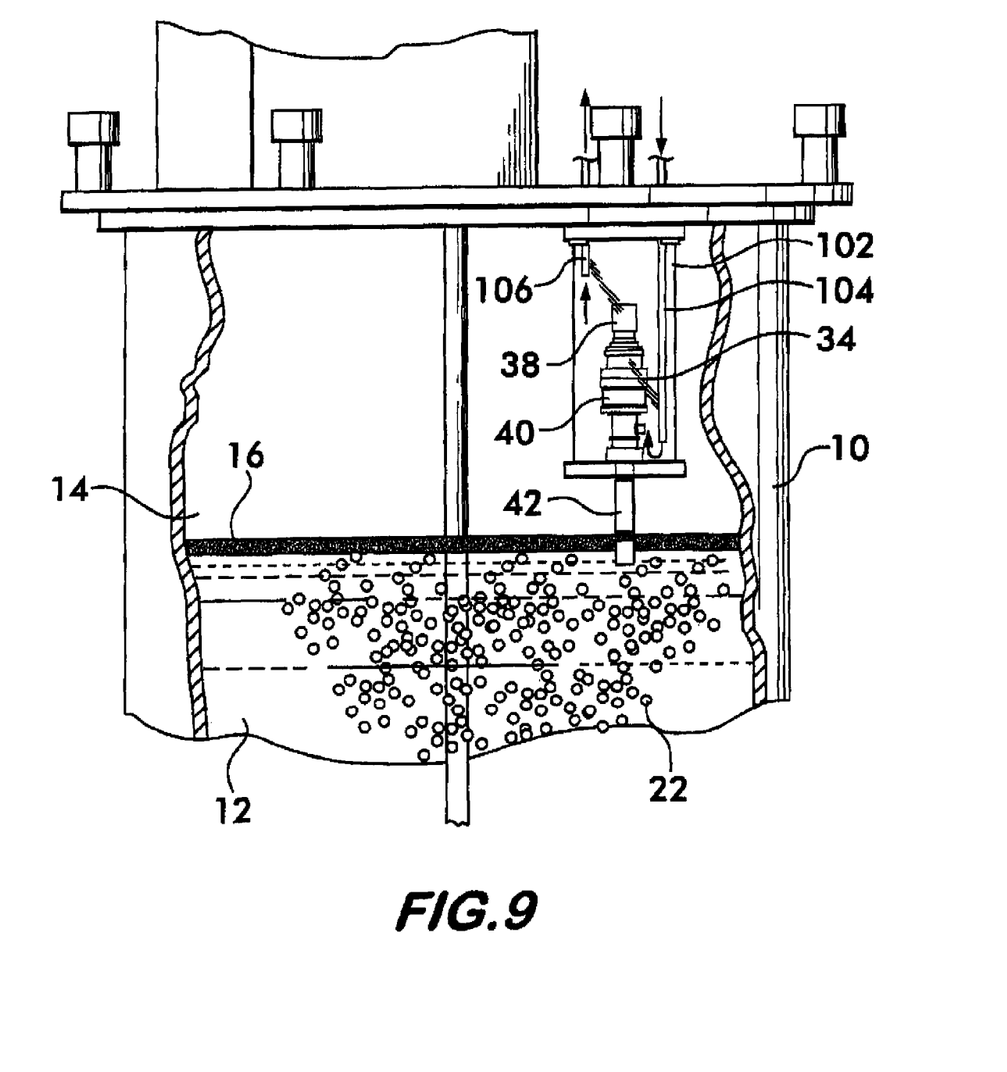
FIG. 9 is a partially-cutaway front elevational view of an upper end of a sealed vessel with a vision probe within a sealed canister according to the present invention.

Preferably, the probe 34 is gas cooled and/or heated to further protect the camera and lens assembly as well as other probe components from processes performed at high and/or low temperatures. As an example, temperatures may reach up to 600° C. within the vessel, and cool gas may be pumped and circulated deep within the probe 34 so that the probe 34 remains operational. As an alternative, the probe 34 can be liquid cooled and/or heated. FIG. 9 illustrates an example of a cooled canister 102 in which a supply of cool air is injected into the distal end of the canister 102 via inlet pipe 104, flows past and cools the lens assembly 40 and camera 38 of the probe 34, and exits the canister via outlet pipe 106 communicating with a proximal end of the canister 102.

The camera 38 can be any device capable of taking or recording still or motion images in any format, and the lens assembly 40 can be provided and adjusted as desired to obtain a desired image. As an example, the camera 38 can record black and white or color images, still images or video images, or can be an infrared camera.

The probe 34 is modular so that different cameras 38 and optical lens assemblies 40 can be readily added or removed from the probe 34 so that a desired image can be obtained. In addition, the probe permits the camera 38 and lens assembly 40 to be interchanged during an on-going process in the vessel 10 without disrupting the process. For instance, a single camera 38 and/or lens assembly 40 can periodically be moved from one access port, 26, 28 and 30, to the next to obtain images from different parts of the vessel 10 during a process or testing procedure. This enables the vision system to be cost effective, since the camera, lens assembly, and various sensors of the probe are typically the most expensive components of the probe. In addition, removal of the camera and lens assembly permits the remainder of the probe to be autoclaved or subjected to chemical sterilization without any concern of damaging the camera 38 and/or lens assembly 40.

The probe 34 includes a distal end 42 interconnected to the proximal end 36. When the probe 34 is mounted to the wall of the vessel 10, the distal end 42 extends through one of the ports, 26, 28 and 30, so that it is located and extends directly within the liquid 12 in the vessel 10. Typically, an O-ring or gasket 108 is provided in a circumferential groove 110 of the distal end 42 and is used for purposes of forming a liquid-tight seal with the port of the vessel 10. A fastening means 112 is used to lock the distal end 42 in place in the port via a threaded connection, snap connection, or the like.

The distal end 42 of the probe 34 is hermetically sealed within a protective shroud 44. Thus, the outside of the shroud 44 can be immersed within the process liquid in the vessel and can prevent the process liquid from entering into the probe 34. Accordingly, the shroud 44 must be able to tolerate the hostile environment within the vessel 10 so that it can protect the other components of the probe 34 from damage. During a process, the shroud 44 remains in place within one of the ports, 26, 28 and 30, and permits other components of the probe 34 to be removed, replaced and/or re-installed without disturbing the process occurring within the vessel 10.

The shroud 44 can be rigid or flexible. For example, the shroud can be a rigid tube of stainless steel, titanium, or other compliant material (see FIGS. 2 and 3). Alternatively, the shroud can have flexible bellows, joints, telescopic sections or the like so that the probe can be articulated or robotically moved to, or pointed at, an area of interest within the vessel during an on-going process. The controls for moving or manipulating the probe can be located external of the vessel. A moveable, flexible probe enables information with respect to a reaction taking place at a particular location within the vessel to be obtained. It can also be used to aim the tip of the probe at a desired angle within the vessel so that the flow of bubbles can be viewed in a desired manner. For instance, an angle or location may be selected that makes it less likely for bubbles or particles to stick to the window of the probe.

Figure 7:
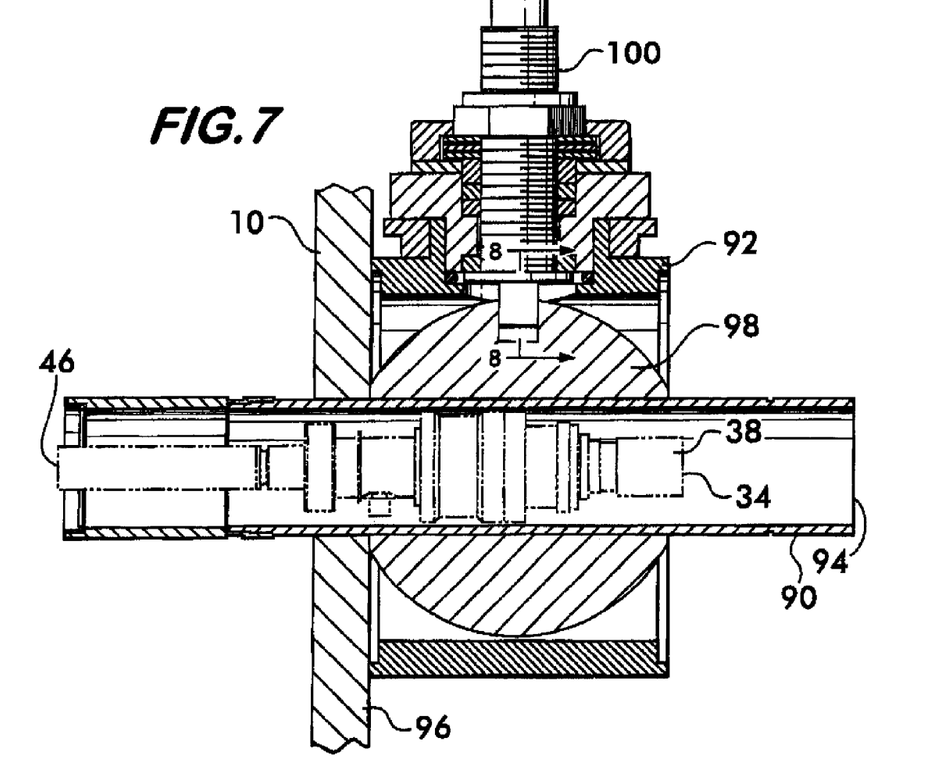
FIG. 7 is a cross sectional view of a ball joint connecting a shroud to a wall of the vessel according to the present invention.
Figure 8:
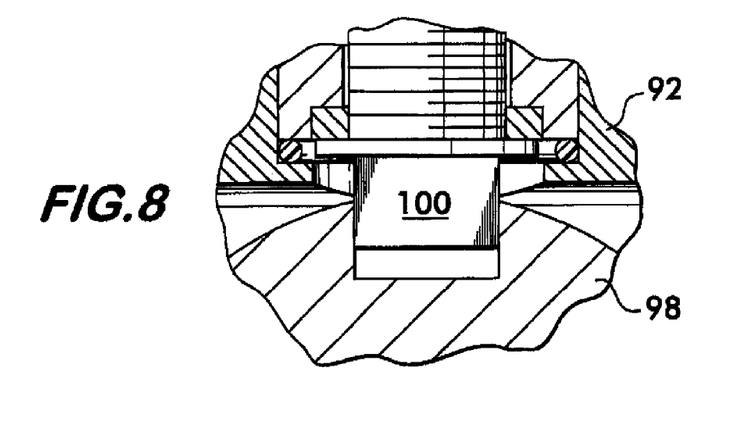
FIG. 8 is a cross-sectional view of a portion of the ball joint along line 8-8 of FIG. 7.

One example of an arrangement permitting the position/orientation of the probe 34 within the vessel 10 to be adjusted without disturbing a process on-going in the vessel 10 is illustrated in FIG. 7. The probe 34 is located within a protective shroud, or canister 90 that is supported by a ball and socket mechanism 92. The canister 90 includes a proximal open end 94 that communicates with ambient conditions external of the vessel 10. The canister 90 extends through an opening in the wall 96 of the vessel 10, and the support mechanism 92 forms a fluid-tight seal about the opening in the wall 96.

The mechanism 92 includes a ball joint 98 that permits the distal end 42 of the probe 34 to be aimed at various locations within the vessel 10. For instance, the ball joint 98 enables the probe 34 to be pointed straight ahead as shown in FIG. 7, or the ball joint 98 can be rotated/pivoted to orient the probe 34 upward at an angle, downward at an angle, to the right, or to the left. Thus, the ball joint 98 can be used for linear motion of the probe 34 or orbital motion. In addition, the probe 34 and/or the canister 90 can be further extended axially into the vessel 10 or be retracted from the vessel 10 to locate the probe 34 closer or further away from the wall 96. The distal end 42 of the probe 34 can extend through an opening in the canister 90 (as illustrated in FIG. 7) or it can be located adjacent a sealed end of the canister which provides a viewing window. The ball and socket mechanism 92 can include a lock 100 for securing the probe in a desired orientation, or for allowing free movement of the ball joint 98 within the mechanism 92. The positioning of the lock 100 can be automatically controlled by a worn gear (not shown) or like control mechanism.

Figure 6:
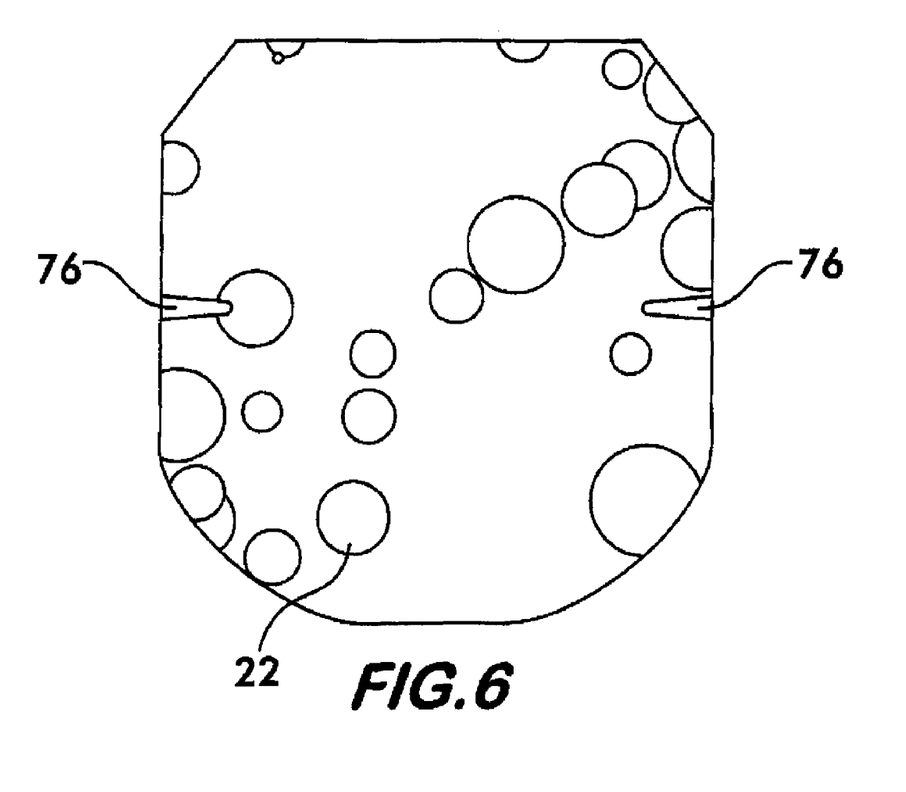
FIG. 6 is an image of bubbles captured by the vision system of the present application.

As best shown in FIG. 2, a high pressure lens, or window, 46 is secured to and seals an opening in the shroud 44 of the probe 34 through which images are recorded by the camera 38. As an example, the lens 46 can be a high purity annealed sapphire window. Alternatively, it can be made of ruby, quartz, glass, or a synthetic material such as polycarbonate. The window 46 can include calibration markings 76 to aid in the determination of the size of the bubbles or particles shown in the recorded images. For example, see the markings 76 in the image provided in FIG. 6. Further, the lens 46 can be a plurality of lenses, for instance, for purposes of widening the viewing angle available to the camera 34.

A transmission media extends longitudinally within the shroud 44 and provides an optical path for the camera 38 from the optical lens assembly 40 to the window 46. For instance, see media 58 in FIG. 3. An example of a transmission media is a coherent fiber optic bundle that transmits images in a coherent manner from one end to the other.

The probe 34 also includes means for directing light from the distal end 42 into the vessel 10. For example, a light source such as provided by light emitting diodes (LEDs) can be provided directly within the probe 34, such as adjacent to the window 46 in the distal end 42 of the probe. Such a light source is modular and can be removed and interchanged with a different light source during an on-going process within the vessel without disrupting the process. Examples of other types of light sources include liquid crystal display (LCD) technology, silicon crystal display (SCD) technology, and laser, halogen, incandescent, and strobe light sources, and light sources which emit different frequencies of light, such as visible light, infrared (IR), and ultraviolet (UV).

An advantage of LEDs is that they can produce light waves within a greater frequency range. For example, LEDs can produce near infrared (IR) light. Such so-called "red light" enables better image resolution in various solutions such as opaque liquids. LEDs that emit ultraviolet (UV) light are also useful since they can provide better penetration. In addition, UV light is also useful for cleaning validation, particularly when the vessel is treated with organic compounds that glow when illuminated with UV light. A strobe light source can be used for stop-action images such as to observe impeller operation, and laser light can be used for back scatter images. Further, since dead cells in a cell culture are typically more transparent than live cells, the frequency of the light or the amount of light can be specifically selected for purposes of better determining whether cells in cell cultures are alive or dead or for other purposes.

As an alternative, a light source can be located externally of the probe. For example, the probe illustrated in FIG. 3 has a light guide 64 that extends longitudinally within the distal end 60 from a light source connector 48 to the window 62 of the probe. The external light source can be connected to the probe, for instance, via a fiber optic line 50 best shown in FIG. 5. The fiber optic line 50 can be random or incoherent for simply transmitting bulk light therethrough. Examples of light guides include fiber optic light guides, liquid light guides, and acrylic light guides.

The distal ends of the probes of the present invention can be provided in different types and can be interchangeable. For example, the distal end 42 of probe 34 is designed to provide back lit images so that bubbles or like particles are silhouetted against light directed toward the camera 38. In the illustrated embodiment, a backscreen 52 is spaced from and faces the window 46 to provide light directed and focused only toward the camera. An opening, or gap, 54 extends transversely through the distal end 42 such that liquid 12 and bubbles 22 can flow directly between the window 46 and the backscreen 52. As an example, the spacing provided by the gap 54 between the backscreen 52 and window 46 can be about 0.125 to about 1.0 inch. The backscreen 52 emits or reflects light thereby enabling the camera 38 to record back lit images of the bubbles. For instance, see the captured image provided in FIG. 6. Illumination of the backscreen 52 can be provided by a light source contained in the backscreen extension 56 or by a light guide extending into the extension 56 via the bridge connection 68. Alternatively, the backscreen 52 can be formed of a reflective material, such as a mirror or ceramic plate, and reflect light being emitted in a forward direction from window 46 back toward the camera 38.

Preferably, the backscreen 52 is a directional light source that emits light focused only toward the camera and does not emit light in all directions within the vessel. The directional light source eliminates the possibility of light reflecting off the walls of the vessel or the like from obscuring or reducing the quality of the images obtained by the camera. Other alternatives include taking images against a dark field or a bright field with back and/or front lighting, or with interference contrast. In addition, the light could be projected from an oblique angle to highlight peaks and valleys within the particles, cells or clumps of bubbles captured in the image.

Figure 3:
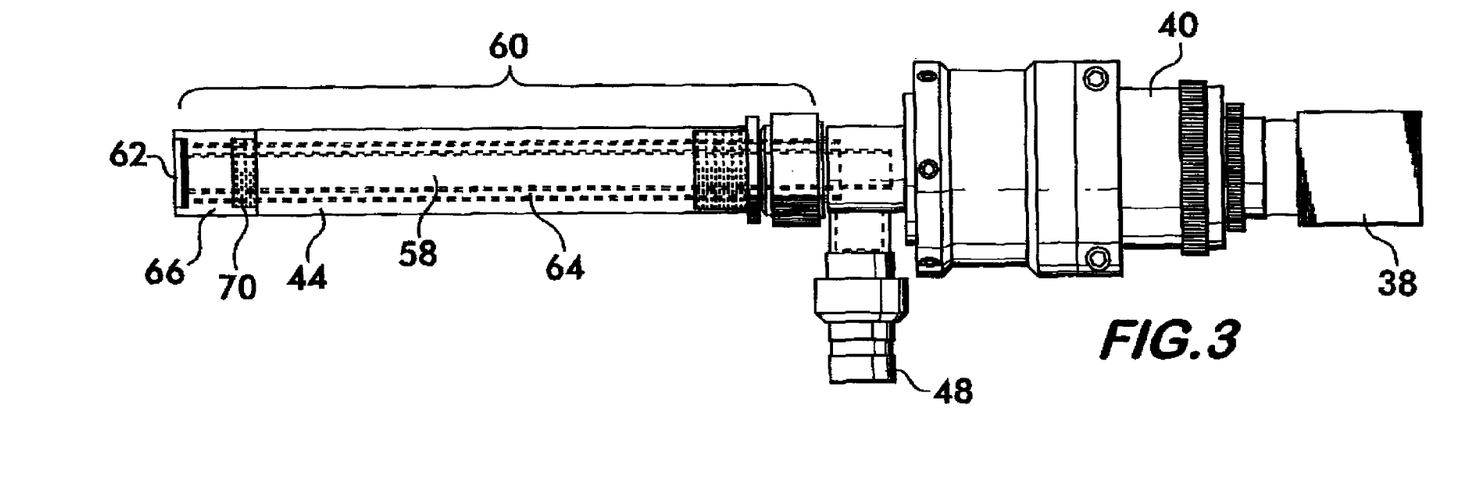
FIG. 3 is a side elevational view of the vision probe with an alternate end tip according to the present invention.

The alternate distal end 60 illustrated in FIG. 3 is best used for recording front lit images, such as images of the headspace and the operation or cleanliness of the agitator, sparger, or interior walls or surfaces of the vessel. As illustrated by dashed lines in FIG. 3, the coherent transmission media 58 for the camera 38 extends centrally throughout the substantially tubular distal end 60 to the window 62. A tubular light guide 64 extends concentrically about the transmission media 58 to transmit bulk light through the distal end 60 and into the vessel 10 in a direction forward of the window 60.

The tip 66 of the distal end 60 is removable and replaceable with other tips of different configurations. For example, tip 66 has a threaded end 70 that can be screwed into or unscrewed from the distal end 60 enabling tip 66 to be replaced with another tip. The other tip, for instance, can extend angularly from the distal end 60 to alter the viewing angle, including a plurality of lenses to effectively widen the viewing angle, or otherwise alter the view provided to the camera 38 by the lens 62. The tip 66 can utilize a prism or other types of lens to adjust the viewing angle or provide a desired view. As an example, instead of a straight optical view path through the distal end 60, the angular tip can alter the path by 5° to 20° or more relative to the longitudinal axis extending through the distal end 60. This enables the camera 38, for instance, to be aimed at hard to clean areas inside the vessel 10 so that these areas can be visually inspected without the expense of disassembling the vessel 10. Typical problem locations may include sidewalls behind splash tube inlets, behind baffles, and the underside of turbine agitators. A tip positioned at a particular angle and location relative to a flow of bubbles within the process liquid may also reduce the likelihood of bubbles sticking to the window of the probe. For instance, a probe tip directed substantially parallel to the flow of gas bubbles may tend to minimize bubbles sticking to the window of the probe. Of course, another alternative for adjusting the viewing angle is provided by ball and socket mechanism 92 discussed above with respect to FIG. 7 of the present application.

The probe 34 can include a fail safe or thermocouple switch that automatically cuts off power to the probe's light source. For example, light sources generate heat and a process ongoing within the vessel may be sensitive to temperature. Accordingly, if too much heat is being generated by the light source, the switch automatically cuts off the light source so as not to affect the process. Typically, processes within fermenters may last several days or weeks. Since images may only need to be obtained once every 30 to 60 minutes, the switch can also control the intervals at which the camera and light source are powered. For example, the switch can power the light source for about 5 seconds every 30 to 60 minutes so that the camera can obtain the desired images. In this manner, the heat generated by the light source will be negligible and a temperature sensitive process can be performed in the vessel. As an alternate, a strobe light source can be used to further minimize heat and/or improve image quality depending upon the image desired.

The camera 38 can be interconnected to a computer processor 72 or the like to view and/or analyze the recorded images in substantially real time. For example, a computer cable 74 or the like can extend from the camera for the automatic transfer of image data from the camera 38 to the computer processor 72. Alternatively, the camera 38 can store images on a storage device (not shown) which can be manually withdrawn from the camera and input into a computer. Yet another alternative is for the image data to be transmitted from the camera 38 via a wireless connection to the computer processor 72. For example, see the wireless systems disclosed in U.S. Pat. Nos. 6,603,117 and 6,723,981 issued to Corrado et al.

Accordingly, the vision system of the present invention can provide remote observation, analysis, verification and historical recording of data of the process occurring within the hostile environment in the vessel and the physical changes occurring therein. Such observations can include observations concerning agitation, aeration, aggregation, foaming, and cleaning.

The computer processor 72 preferably includes image recognition and analysis software. The software can be used to provide element and constituent analysis and measurements of bubble size, mean diameter, surface area, volume, flow rate, flow pattern, population, distribution, rate of reduction, color, Sauter mean, the ratio of surface area of bubbles relative to volume of bubbles, gas hold-up ratio of gas volume to volume of liquid, and interfacial area (i.e., amount of surface area of bubbles in direct contact with liquid). An example of an image of bubbles is provided in FIG. 6. The analysis provided by the software can be used to adjust process parameters of an on-going process within the vessel 10. For example, the gas flow rate through the sparger 18 and/or the RPMs of the agitator 24 can be adjusted. A strobe light source can be used in the case of monitoring RPMs of the agitator 24.

Figure 4:
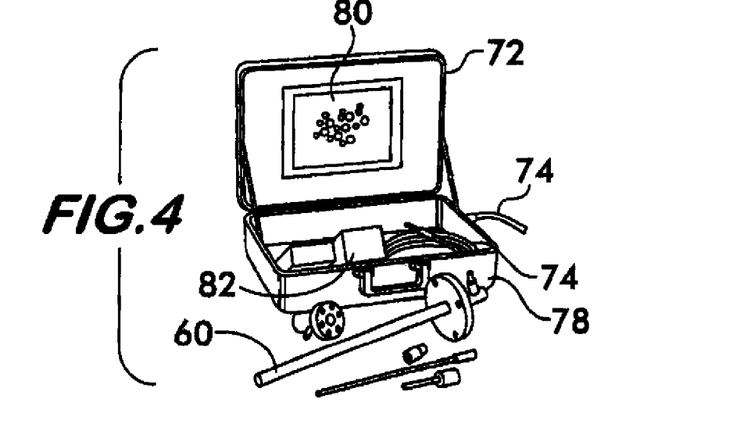
FIG. 4 is a perspective view of portable components of the modular vision analysis system according to the present invention.
Figure 5:
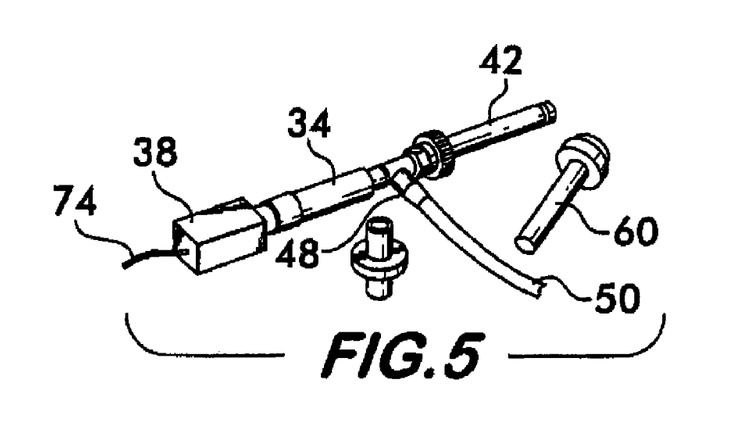
FIG. 5 is a perspective view a modular vision probe with interchangeable parts according to the present invention.

In the embodiments illustrated in FIGS. 4 and 5, the present invention is provided as a portable kit. For example, as shown in FIG. 4, a carrying case 78 for the various components of the probes also includes a computer processor and screen 80. Image recognition and analysis software is loaded in the processor of the carrying case 78. In addition, a light source 82, cables 74, and various interchangeable components of the vision probe are carried within the case 78. Such components can include, for instance, an articulating shroud or ball and socket mechanism 92 (see FIG. 7), various different types of internal and external light sources, and wireless transmitters/receivers. As best shown in FIG. 5, the probe can be provided with interchangeable distal ends. For example, distal end 42 can be utilized where back lit images are desired, and distal end 60 can be used where front lit images are desired. In addition, the camera 38 is removable from the probe and can be moved to another probe at another location on the vessel 10, or the cable 74 from one camera can be connected to another camera at a different location on the vessel 10.

The vision probes can also carry sensors, such as in the distal end of the probe. The sensors can include temperature sensors, pressure sensors, oxygen sensors, spectrographic chemical analysis sensors, and the like. The sensors can be non-contact, optical, point-and-shoot type sensors that take readings at a focal point of the sensors. Thus, the sensors do not necessarily need to be in direct contact with the process fluid. This enables the sensors to be moved from one probe to another during a process without disturbing the process. In addition, the sensors can be interchangeable so that the user can determine which sensor or sensors are required for a particular process or procedure. Further, the sensors can be aimed at various locations within the vessel to provide information with respect to different locations in the vessel. Information from the sensors can be fed automatically to the computer processor 72 for analysis, verification, and/or recording. Such information can also be used to automatically adjust process parameters of the process occurring within the sealed vessel.

The present invention also relates to a method of analyzing bubbles or other small particles in a process liquid contained in a sealed or unsealed vessel. With respect to bubbles, gas is released from a sparger in a process liquid within a sealed vessel. Preferably, the gas bubbles within the process liquid are distributed and sheared within the liquid by an agitator located adjacent the sparger. The gas bubbles are observed in-situ with at least one vision probe extending through one or more access ports in the walls of the vessel.

The vessel preferably has multiple access ports located at different locations for enabling different areas within the vessel to be observed. The vision probes are mounted within the access ports and include interchangeable parts (camera, lens assembly, sensors, light guide or source, articulating shrouds or canisters, ball and socket joints, etc.) permitting the user to obtain a desired observation and/or to share different components among the various ports.

The bubbles or other particles are observed by projecting light from the vision probe into the vessel to illuminate the gas bubbles or particles and by recording images of the illuminated bubbles or particles with a camera mounted on a proximal end of the probe. The light source can provide continuous, intermittent, or strobe lighting at various frequencies of light. Preferably, the camera is located on the ambient side of the vessel wall and can be periodically moved from one probe to the next allowing observations to be made at different locations within the vessel without disrupting an ongoing process in the vessel. Alternatively, the probe 34 can extend within the vessel 10 in a sealed canister 102 as shown in FIG. 9. In this case, the probe 34 is protected from the environment within the vessel 10 by the canister 102, and the environment within the canister can be pressurized, heated, cooled and/or in communication with ambient atmosphere for purposes of protecting the camera 38 and lens assembly 40. As another alternative, the probe 34 can simply be mounted via a bracket or the like within an open top of a vessel above the process liquid.

The canister 102 can be rotatable or movable so that the location of the end tip of the probe 34 within the vessel can be altered to provide information about different locations within the vessel 10. If backlit or silhouette images of the bubbles or particles are desired, the probe can be provided with a distal end that emits or reflects light from behind the gas bubbles or particles toward the direction of the camera. Alternatively, the distal end can be designed to project light forward of the distal end so that front lit images can be obtained.

The recorded images are preferably transferred to a computer processor or the like having image recognition and analysis software. Such software analyzes the images and determines information therefrom concerning the ongoing process or the mechanical operation or cleanliness of the vessel. For example, the software can make measurements of bubble size, mean diameter, surface area, flow rate, flow pattern, population distribution, Sauter mean, the ratio of surface area of bubbles relative to volume of bubbles, gas hold-up ratio of gas volume to volume of liquid, and interfacial area (i.e., amount of surface area of bubbles in direct contact with liquid) or the like. This information can be provided in substantially real time so that corrective adjustments can be made to an ongoing process within the vessel.

If desired, the headspace of the vessel can be observed to determine foam characteristics, such as level, thickness, color, density and bubble size. In addition, probes can be used to provide visual inspection of agitation or aeration conditions, mechanical motion of said agitator, or cleanliness of said vessel. This inspection can take place without disassembling the vessel or disrupting an ongoing process or testing procedure taking place within the vessel. Further, a temperature or pressure of the process liquid or a chemical analysis of the process liquid can be obtained via one or more sensors carried on the distal end of the probe.

The above-described vision analysis systems and methods according to the present invention provide a modular vision system permitting in-situ observation of conditions within a seated or unsealed vessel. The vision probes include interchangeable parts permitting different types of images to be recorded at various locations within the sealed vessel. The ability to share expensive components, such as cameras, lens assemblies, and sensors, minimizes system costs while maximizing system versatility. The observation, analysis and measurements provided by the vision analysis system enables the user to manually or automatically anticipate problems and take preventive action to adjust the parameters of an on-going process to maximize the effectiveness of the process.

While preferred vision analysis systems and methods have been described in detail, various modifications, alterations, and changes may be made without departing from the spirit and scope of the present invention as defined in the appended claims.

The invention claimed is:

1. A remote vision analysis system, comprising:
a vessel containing a process liquid having gas bubbles or particles therein;
a sparger extending within said vessel for releasing gas in the form of bubbles directly into the process liquid;
an agitator located adjacent said sparger within said vessel;
a probe having an elongate distal end extending within an interior of said vessel and a proximal end including a camera for recording images of the process liquid, gas bubbles or particles, or surfaces within said vessel thereby enabling in-situ observation of the process liquid, gas bubbles or particles, or surfaces within said vessel, said distal end having a lens through which images are recorded by said camera;
a light source or light guide located in said distal end of said probe for projecting light into said process liquid within said vessel;
a protective shroud for housing said probe and hermetically-sealing said probe from said process liquid within said vessel;
a switch for automatically cutting off power from said light source or light guide when temperature within said shroud exceeds a pre-set temperature or for turning power to said light source or light guide on and off at pre-set intervals to limit heat generated by said light source or light guide; and
a computer processor having image recognition and analysis software, said camera being interconnected to said processor for transferring said images in substantially real time to said processor for analysis by said software in substantially real time.

2. A remote vision analysis system, comprising:
a vessel containing a process liquid having gas bubbles or particles therein;
a sparger extending within said vessel for releasing gas in the form of bubbles directly into the process liquid;
an agitator located adjacent said sparger within said vessel;
a probe having an elongate distal end extending within an interior of said vessel and a proximal end including a camera for recording images of the process liquid, gas bubbles or particles, or surfaces within said vessel thereby enabling in-situ observation of the process liquid, gas bubbles or particles, or surfaces within said vessel, said distal end having a lens through which images are recorded by said camera;
a light source or light guide located in said distal end of said probe for projecting light into said process liquid within said vessel;
a protective shroud for housing said probe and hermetically-sealing said probe from said process liquid within said vessel; and
a computer processor having image recognition and analysis software, said camera being interconnected to said processor for transferring said images in substantially real time to said processor for analysis by said software in substantially real time;
said distal end of said probe having a backscreen spaced from and facing said lens, said probe including a transversely disposed opening that permits the process liquid and gas bubbles to flow directly between said backscreen and said lens, and said backscreen emitting or reflecting light directed and focused toward said camera.

3. A remote vision analysis system, comprising:
a vessel containing a process liquid having gas bubbles or particles therein;
a sparger extending within said vessel for releasing gas in the form of bubbles directly into the process liquid;
an agitator located adjacent said sparger within said vessel;
a probe having an elongate distal end extending within an interior of said vessel and a proximal end including a camera for recording images of the process liquid, gas bubbles or particles, or surfaces within said vessel thereby enabling in-situ observation of the process liquid, gas bubbles or particles, or surfaces within said vessel, said distal end having a lens through which images are recorded by said camera;
a protective shroud for housing said probe and hermetically-sealing said probe from said process liquid within said vessel;
a light source or light guide located in said distal end of said probe, said light source or light guide being a discrete continuous, intermittent or strobe light source for projecting light into said process liquid within said vessel, said discrete light source being removable from said shroud during an on-going process in said vessel without disrupting the process and being interchangeable with a different light source; and
a computer processor having image recognition and analysis software, said camera being interconnected to said processor for transferring said images in substantially real time to said processor for analysis by said software in substantially real time.

4. A remote vision analysis system according to claim 3, wherein said orientation or position of at least one of said shroud and probe are re-positionable within said vessel during an on-going process.

5. A remote vision analysis system according to claim 4, wherein said shroud extends through a ball and socket mechanism that enables movement thereof relative to a wall of said vessel.

6. A remote vision analysis system according to claim 3, further comprising a plurality of interchangeable end tips for said distal end of said probe, said end tips including end tips that alter a viewing angle within said vessel, end tips that widen a viewing angle, end tips enabling front lit images to be taken, and end tips enabling back lit images to be taken.

7. A remote vision analysis system according to claim 3, wherein said vessel is defined by walls that include a plurality of access ports in which said probe is removably mountable or an open top in which said probe is removably mountable.

8. A remote vision analysis system according to claim 7, wherein said ports include a port located on said vessel to permit observation of headspace within said vessel, a port located on said vessel to permit observation of or adjacent to said agitator, and a port located on said vessel to permit observation of or adjacent to said sparger.

9. A remote vision analysis system according to claim 8, wherein said probe is installable within and removable from any of said ports.

10. A remote vision analysis system according to claim 7, wherein a probe is located within each of said ports and wherein a camera is shared by said probes such that the camera can be periodically disconnected from one probe and reconnected to another.

11. A remote vision analysis system according to claim 3, further comprising a non-contact optical sensor carried by said distal end, said sensor being selected from the group consisting of a temperature sensor, a pressure sensor, and chemical analysis sensor.

12. A remote vision analysis system, comprising:
a vessel containing a process liquid having gas bubbles or particles therein;
a sparger extending within said vessel for releasing gas in the form of bubbles directly into the process liquid;
an agitator located adjacent said sparger within said vessel;
a probe having an elongate distal end extending within an interior of said vessel and a proximal end including a camera for recording images of the process liquid, gas bubbles or particles, or surfaces within said vessel thereby enabling in-situ observation of the process liquid, gas bubbles or particles, or surfaces within said vessel, said distal end having a lens through which images are recorded by said camera;
a light guide located in and extending longitudinally through said distal end of said probe for projecting light into said process liquid within said vessel;
a protective shroud for housing said probe and hermetically-sealing said probe from said process liquid within said vessel; and
a computer processor having image recognition and analysis software, said camera being interconnected to said processor for transferring said images in substantially real time to said processor for analysis by said software in substantially real time;
said proximal end of said probe including an optical lens assembly located between said camera and said distal end, said elongate distal end including a coherent fiber optic bundle extending from said optical lens assembly to said lens in said distal end, and said light guide extending concentrically about said coherent fiber optic bundle.

13. A method of analyzing bubbles in a process liquid contained in a vessel, comprising the steps of:
releasing gas in the form of bubbles from a sparger in the process liquid within the vessel;
agitating the process liquid with an agitator located adjacent said sparger;
mounting multiple probes to the vessel at different locations and using a single camera shared by said multiple probes such that the camera is periodically disconnected from one probe and connected to another probe during a process occurring within the vessel without disrupting said process; and
observing the gas bubbles in-situ with at least one of said probes which extends through a wall of said vessel.

14. A method according to claim 13, further comprising the step of re-positioning at least one of said probes and/or its orientation within the vessel during an on-going process to observe a different region within said vessel.

15. A method according to claim 13, wherein said observing step includes projecting light from at least one of said probes into said vessel to illuminate said gas bubbles and recording images of said illuminated bubbles with the camera mounted on said at least one probe.

16. A method according to claim 15, further comprising the step of analyzing said images with image recognition and analysis software in substantially real time, and wherein said analyzing step includes measuring at least one of bubble size, mean diameter, surface area, flow rate, flow pattern, population distribution, Sauter mean, gas hold-up ratio, and interfacial area.

17. A method according to claim 16, further comprising the step of controlling a process condition in the vessel based on said analyzing step.

18. A method according to claim 17, wherein said step of controlling includes adjusting gas flow rate through the sparger or adjusting a rate of rotation of the agitator.

19. A method according to claim 13, further comprising the step of visually observing headspace, foam characteristic, or foam level at the top of the vessel or visually inspecting agitation or aeration conditions, mechanical motion of said agitator, or cleanliness of said vessel with at least one of said probes.

20. A method according to claim 13, further comprising the step of sensing a temperature or pressure of the process liquid with an on-contact, optical, point-and-shoot sensor carried in the distal end of at least one of said probes.

* * * * *